United States Patent [19]

Anderson et al.

[11] Patent Number: 5,764,142
[45] Date of Patent: Jun. 9, 1998

[54] FIRE ALARM SYSTEM WITH SMOKE PARTICLE DISCRIMINATION

[75] Inventors: Donald D. Anderson, Easton, Conn.; Lee Tice, Bartlett, Ill.

[73] Assignee: Pittway Corporation, Chicago, Ill.

[21] Appl. No.: 583,605

[22] Filed: Jan. 5, 1996

Related U.S. Application Data

[63] Continuation-in-part of Ser. No. 522,599, Sep. 1, 1995.
[51] Int. Cl.⁶ .................................................. G08B 29/00
[52] U.S. Cl. .................... 340/511; 340/506; 340/517; 340/519; 340/556; 340/630; 340/825.06; 340/525.07; 340/514
[58] Field of Search .................. 340/501, 517, 340/506, 519, 511, 825.06, 825.07, 514, 522, 526, 555, 556, 628, 630

[56] References Cited

U.S. PATENT DOCUMENTS

| | | |
|---|---|---|
| 5,132,548 | 7/1992 | Borden et al. |
| 5,155,468 | 10/1992 | Stanley et al. ............ 340/501 |
| 5,471,194 | 11/1995 | Guscott ..................... 340/511 |
| 5,477,218 | 12/1995 | Mammoto et al. ......... 340/630 |

FOREIGN PATENT DOCUMENTS

| | | |
|---|---|---|
| 0 076 338 | 4/1983 | European Pat. Off. |
| 0 290 413 | 11/1988 | European Pat. Off. |
| 0 462 642 | 12/1991 | European Pat. Off. |
| 0 530 723 | 3/1993 | European Pat. Off. |
| 52-135297 | 12/1977 | Japan . |
| 2 151 384 | 7/1985 | United Kingdom . |
| WO 89/04032 | 5/1989 | WIPO . |
| WO 95/29393 | 11/1995 | WIPO . |

*Primary Examiner*—Jeffery Hofsass
*Assistant Examiner*—Daryl C. Pope
*Attorney, Agent, or Firm*—Dressler, Rockey, Milnamow & Katz

[57] ABSTRACT

A fire detection system provides multiple levels of signal processing so as to minimize the effects of noise from various sources. In a first level of processing any DC bias in signals received from detectors is removed. In a second level of processing, signal values from current sample times for a given detector are compared to one or more prior sample values from that detector for purposes of removing large transient pulses due to dust particles and the like. In a third level of processing, high frequency noise, perhaps from electrical sources, is filtered from the representation of the signal. Finally, the fully processed signal value is compared to one or more threshold values so as to make a determination as to the presence or absence of a pre-alarm or a fire condition.

31 Claims, 9 Drawing Sheets

FIG. 7A DETECTOR OUTPUT

FIG. 7B PROCESSED OUTPUT

FIG. 7C PROCESSED OUTPUT

FIG. 8

FIRE ALARM SYSTEM WITH SMOKE PARTICLE DISCRIMINATION

This is a continuation-in-part of Ser. No. 08/522,499 filed on Sep. 1, 1995, entitled: "PRE-PROCESSOR APPARATUS AND METHOD".

FIELD OF THE INVENTION

The invention pertains to the suppression of random noise on electrical signals received from ambient condition sensors. More particularly, the invention pertains to processing apparatus and methods for minimizing random noise variations in electrical signals indicative of ambient conditions such as smoke or fire.

BACKGROUND OF THE INVENTION

Various systems are known for the detection of alarm conditions. One particular form of such a system is a smoke or fire detecting system of a type generally illustrated in previously issued Tice et al. U.S. Pat. No. 4,916,432, assigned to a common assignee and incorporated herein by reference. The parent application Ser. No. 08/522,599 is also assigned a common assignee and is also incorporated herein by reference.

Upon receipt of inputs from one or more of the detectors of the system, a control unit associated with the system is able to make a determination as to whether or not a fire condition is present in one or more reasons of interest. A variety of techniques have been used in the past for the purpose of making this determination.

Sensors of smoke such as photoelectric smoke detectors or ionization-type smoke detectors are intended to provide outputs indicative of sensed levels of ambient smoke. Environmental noise, such as dust particles or insects which may enter the respective detector can produce variations in output signals from the sensors which are not in any way correlated with the presence of smoke. These noise outputs can produce false alarms if the sensitivity of the respective detector is high enough. Such false alarms are undesirable.

Prior attempts at addressing this problem have been successful only in part. Screens have been used in detectors to block the entry of insects into the unit. The sensitivity of a given detector can be reduced thereby requiring larger output signals to produce a false alarm condition, (also larger output signals to produce a true alarm condition). This is a less than desirable solution since it will delay the generation of an alarm signal in the presence of smoke or fire. Alternately, some form of filtering or smoothing of the output signal, either analog or digital, can be used for purposes of reducing the effects of such random transient noise.

Nevertheless, there continues to be a need for improved apparatus and techniques for minimizing the effects of random noise so that detectors can be operated with the highest possible sensitivity yet still be sufficiently immune from false alarming due to noise transients. Preferably, such apparatus and methods could be incorporated into detectors without significantly increasing the complexity or the expense thereof.

SUMMARY OF THE INVENTION

Detector chamber signals are caused by the light-scattering effect of particles passing through a very small but very intense light beam. Non-smoke particles, such as dust and lint, are relatively sparse and relatively large compared to smoke particles.

A photo detector in accordance with the present invention combines a short effective beam length with a small diameter beam. This results in a beam sensing volume on the order of 10% that of prior detectors.

Because of the especially small volume of the light-scattering region, and because the particles are constantly in motion, non-smoke particles with usually reside in the small light-scattering volume for only a short period of time, therefore they provide a transient signal. Since smoke particles are much smaller and are much more numerous in the light-scattering volume, they provide a relatively continuous signal.

The characteristics of these transient signals can be used as a basis for distinguishing between these noise signals and a smoke induced signal. Once it is possible to reliably discriminate noise signals from the smoke signals it becomes possible to operate the detectors at higher sensitivity levels without undue increases in false alarms. The consequence of such high sensitivity operation is that small, slow burning fires can more readily be detected.

An apparatus to process an output signal from an ambient condition sensor can be located at or remote from the sensor. The processing apparatus removes noise pulses which are not correlated with an ambient condition being sensed.

In one embodiment, software in a remotely located control panel can be used to differentiate the transient signals from the continuous smoke signals. A fire alarm system so constructed is capable of detecting very low levels of smoke without false alarms caused by non-smoke signals, such systems therefore provide much earlier warning of a fire than systems not so constructed.

In addition, prior to removal of the dust induced noise, any existing DC bias can be removed. Finally, after the effects due to dust induced noise have been removed, the remaining signal can be further processed to eliminate high frequency noise.

The processed signal can then be subjected to fire analysis. It can also be compared to one or more thresholds to make a fire determination.

Processing to remove dust-type distortions can be carried out by comparing the present output value from the sensor to a prior output value and selecting a minimum value therebetween. The apparatus can incorporate storage for two prior values and the present output value can be compared to two prior values and a minimum of the three values selected.

Additional processing can be carried out by comparing the present output value to a nominal expected output value. If the present value exceeds the nominal expected output value, a minimum is selected among the present output value and one or more prior values. If the present output value is less than the nominally expected value, a maximum is selected from among the present output value and one or more prior output values.

A processing method in accordance with the present invention includes the steps of:

(a) detecting a current value of an ambient condition and generating a signal indicative thereof;

(b) removing any DC bias in the signal;

(c) removing any dust-induced distortions;

(d) removing any high frequency noise present on the signal; and (e) processing the signal to determine if a fire condition is present.

Numerous other advantages and features of the present invention will become readily apparent from the following

DETAILED DESCRIPTION OF THE PREFERRED EMBODIMENT

While this invention is susceptible of embodiment in many different forms, there are shown in the drawing, and will be described herein in detail, specific embodiments thereof with the understanding that the present disclosure is to be considered as an exemplification of the principles of the invention and is not intended to limit the invention to the specific embodiments illustrated.

Figure 1:
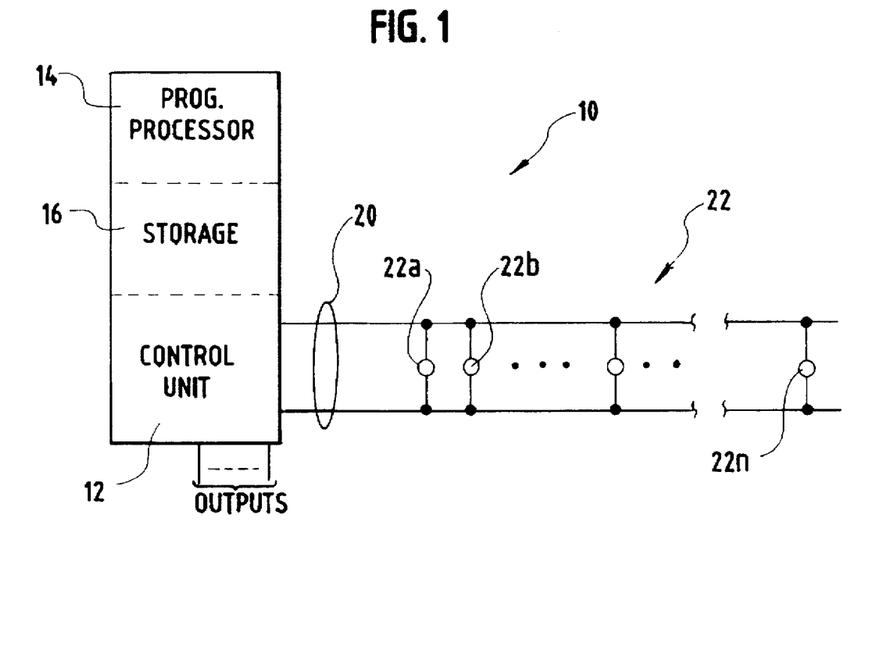
FIG. 1 is a block diagram of an alarm system in accordance with the present invention.

FIG. 1 illustrates a block diagram of a system 10 in accordance with the present invention. This system 10 includes a control unit 12, which can be implemented with a programmable processor 14 and a storage unit 16. The storage unit 16, which can be implemented using read-only storage, read/write storage or electrically programmable read-only storage, can include both control programs and data storage regions for use by the processor 14.

The control unit 12 is coupled by a bidirectional communication link 20 to a plurality of ambient condition sensors or detectors generally indicated at 22. The members of the plurality 22, such as sensors 22a, 22b–22n are intended to detect a particular ambient condition in an adjacent region.

The control unit 12 also includes a plurality of outputs. The outputs can be used to activate audible or visual alarms. In addition, the unit 12 can be coupled to ventilation or air handling systems in the building so as to control smoke migration.

Representative types of detectors include ionization-type or photoelectric-type smoke detectors. Temperature sensors as well as other types of ambient condition sensors could be used in the system 10 in accordance with the present invention.

Figure 2:
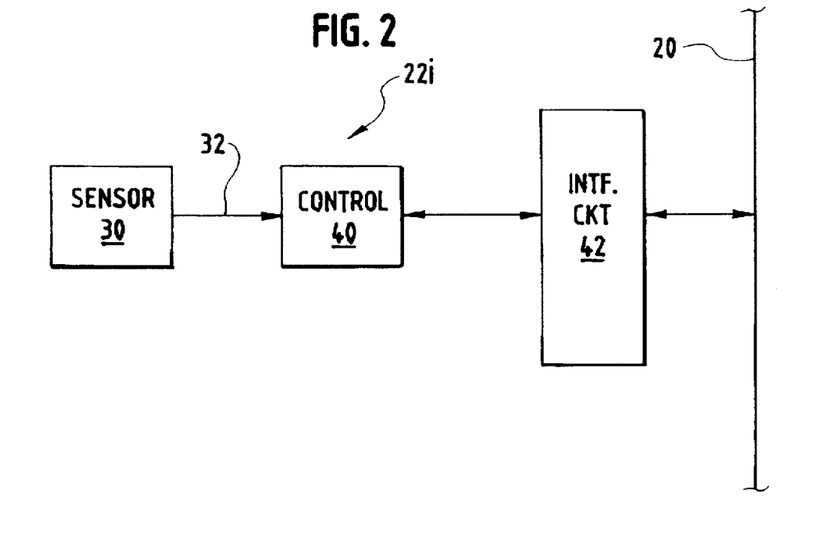
FIG. 2 is a block diagram of a detector usable with the alarm system of FIG. 1.

FIG. 2 is a block diagram representation of a detector 22i useable with the system 10. The detector 22i, includes a sensor element 30. The element 30 is intended to sense a particular ambient condition, such as smoke, temperature, infrared radiation or the like and it generates an electrical system indicative thereof on a line 32.

Referring again to FIG. 2, output from the sensor 30, on the line 32 is coupled to a local detector control element 40. The control element 40 could be implemented with either digital or analog circuitry. If in digital form, the control element 40 could be implemented as either hard wired logic or could incorporate a programmed microprocessor. The control element 40, via interface circuitry 42 is capable of carrying on bidirectional communication with the system control unit 12, via the communication link 20.

A method in accordance with the present invention, to be described subsequently, could be implemented in either the system control unit 12 or the detector local control element 40 without limitation. Implementation can be by either hardwired circuitry or by means of a programmed microprocessor also without limitation.

Figure 2A:
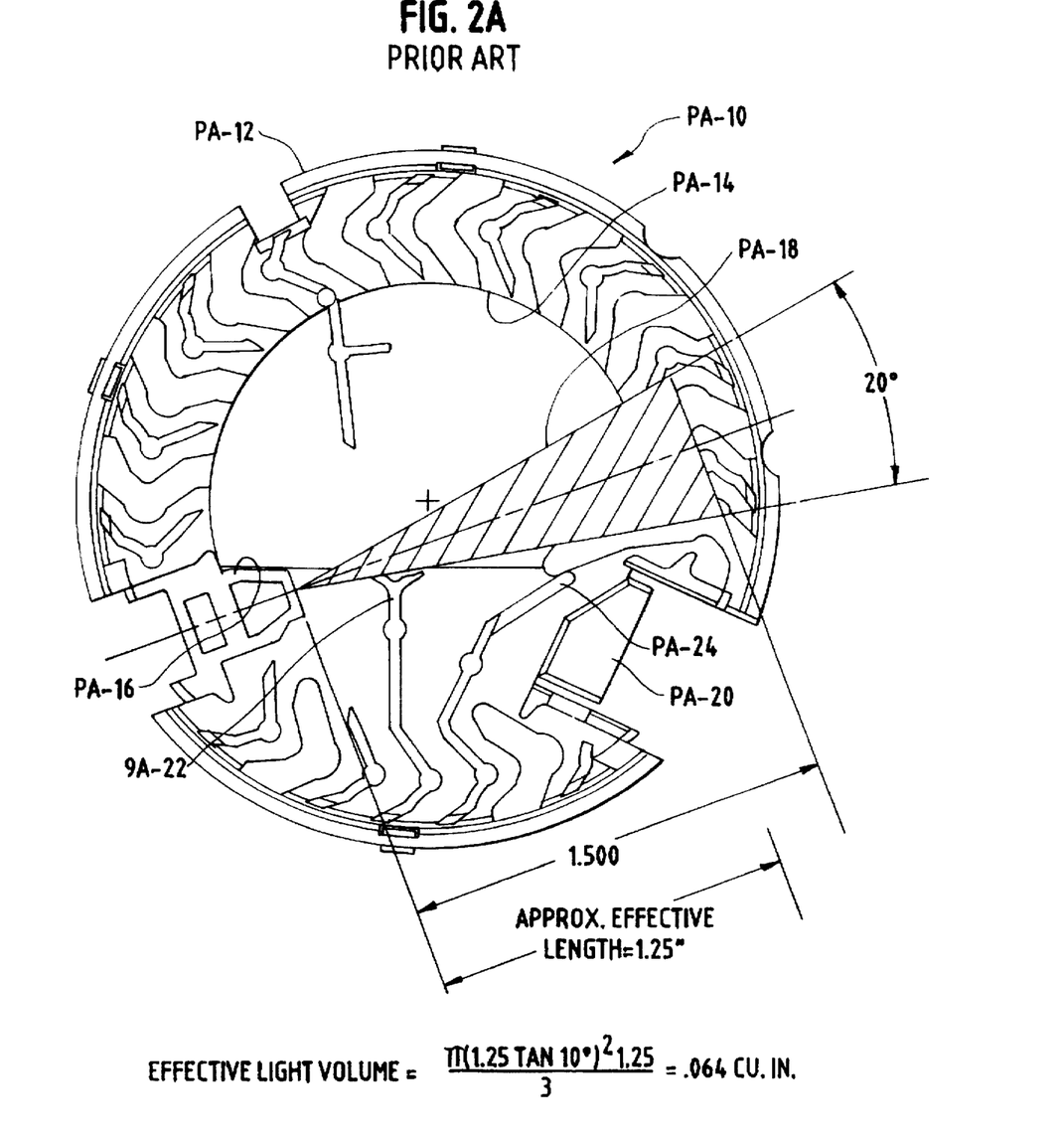
FIG. 2A is a sectional view of a prior art photoelectric detector.

FIG. 2A illustrates in cross-section, a prior art photoelectric chamber PA-10. This chamber includes a housing PA-12 with an internal sensing volume PA-14.

A light emitting source, PA-16 is carried on the housing and oriented to emit a beam of light PA-18 into the internal light sensing region PA-14. As is illustrated in FIG. 2A, the emitted light beam PA-18 exhibits a somewhat conical expanding shape as it traverses the region PA-14. The light beam PA-18 is directed toward a light absorbing trap also carried on the housing PA-12.

Offset from the axis of the beam PA-18 is a photoelectric sensor PA-20. The sensor PA-20 is oriented such that light from the beam PA-18 which has been scattered by particulate matter in the volume PA-14 will be incident thereon thereby generating an output electrical signal.

Elements PA-22 and PA-24 limit the amount of light which can fall upon the sensor PA-20.

The effective sensing light volume for the geometry of the chamber PA-10 is on the order of 0.064 cubic inches.

Figure 2B:
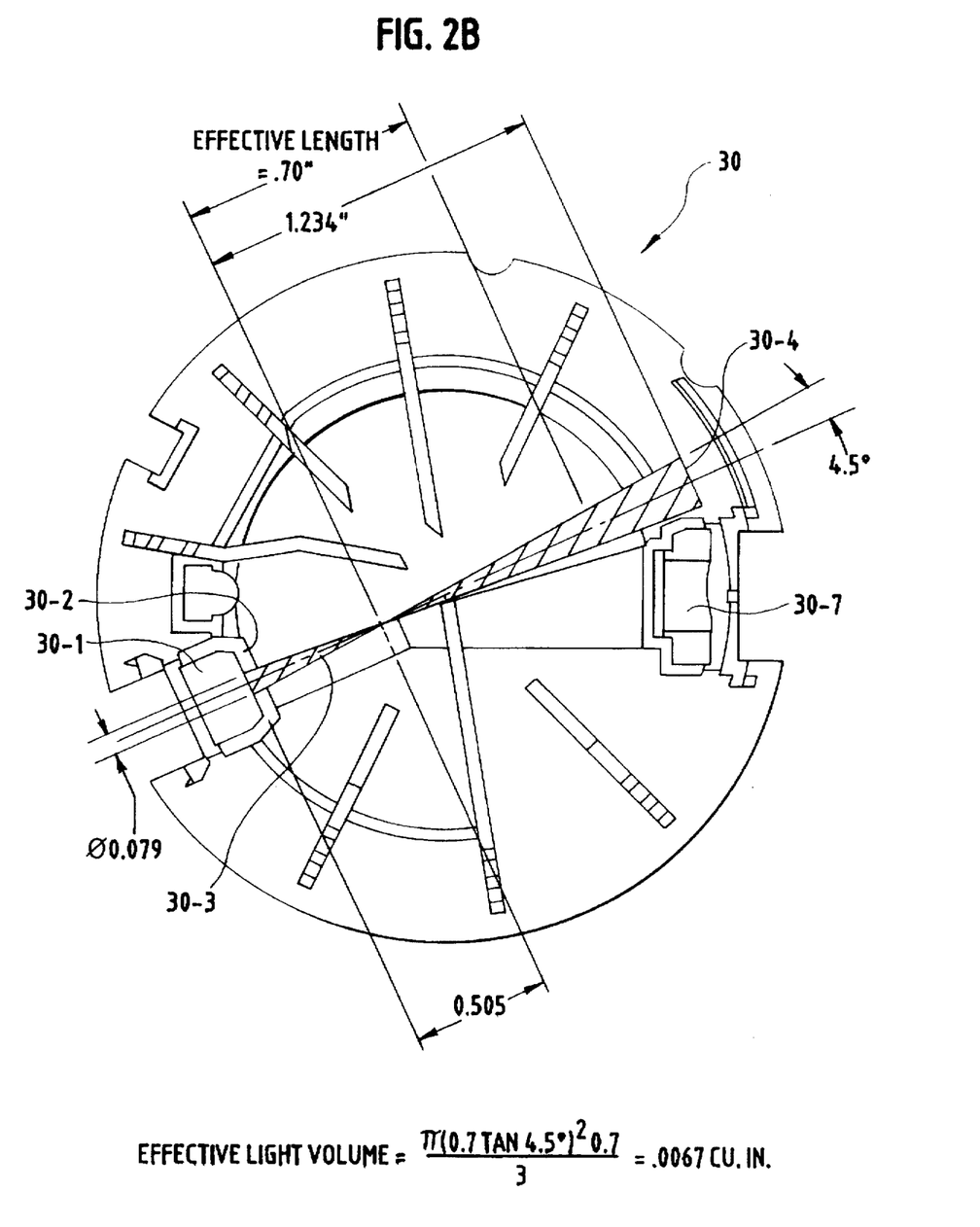
FIG. 2B is a sectional view of a photoelectric detector in accordance with the present invention.

FIG. 2B is a cross-sectional drawing of a smoke sensing chamber 30 of a representative smoke detection device such as 22i in accordance with the present invention. The housing 30 could, for example, have a diameter on the order of three inches or less. For example, a housing with a diameter on the order of two and one-half inches or less could be used.

A high intensity source of coherent light 30-1, such as a laser or a laser diode, is carried by the housing or chamber 30. The light source is pulsed to cause it to emit a short pulse of light at periodic intervals (every few seconds).

A lens 30-2 focuses the light into a small but intense cylindrical beam 30-3. The light beam 30-3 continues through the detector chamber until it strikes a light trap 30-4 at the opposite end of the chamber. The light trap absorbs most of the light, and reflects a small amount away from the central chamber area.

Preferably, source 30-1 in combination with the lens 30-2 will produce a beam 30-3 having an effective beam or light sensing volume on the order of 0.0067 cubic inches. This beam volume is on the order of 10% that of prior art detectors.

Hence, dust particles are large compared to the diameter and volume of the beam 30-3. The dimensions of light beam 30-3 as well as those of the sensing beam volume are smaller than a typical distance between ambient dust particles. As described subsequently, this reduced volume makes the detector 30 less likely to produce dust induced output signals which appear to be due to the presence of smoke.

Figure 3:
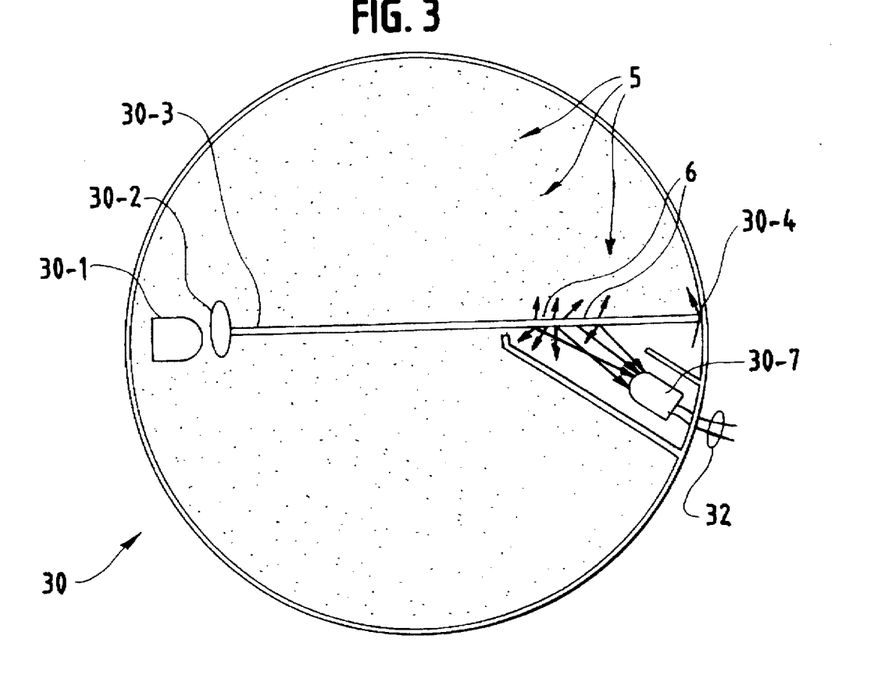
FIG. 3 is a schematic view of the photoelectric detector of FIG. 2B illustrating smoke effects.
Figure 4:
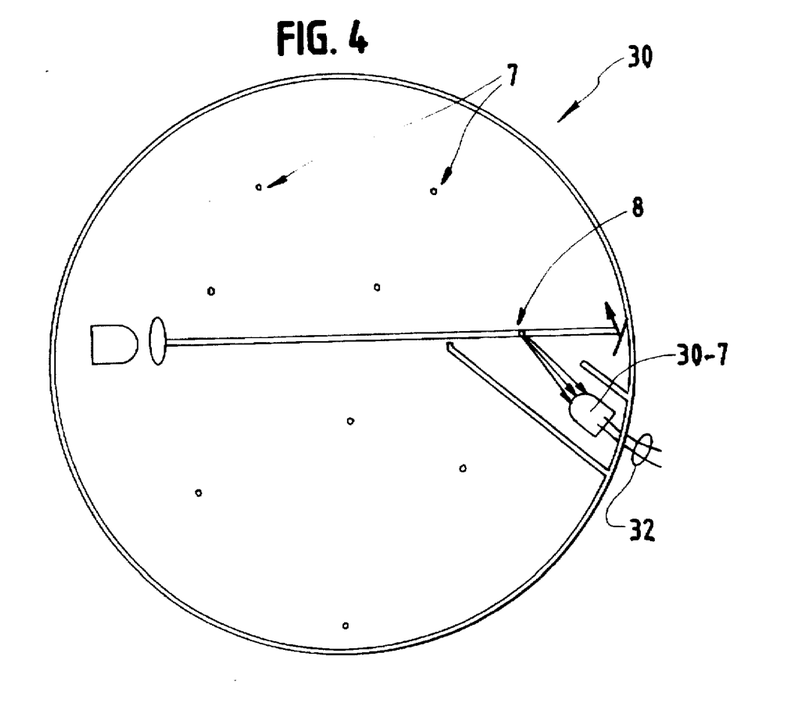
FIG. 4 is a view of the detector of FIG. 3 illustrating dust effects.

FIGS. 3 and 4 are schematic representations of the detector 30 of FIG. 2B.

Small smoke particles 5 are shown residing at many points throughout the air in the detector chamber. Smoke particles 6 in the central area of the light beam scatter some of the light at all angles.

A light sensor 30-7, such as a photo diode, is placed at an angle to the axis of the light beam so that light signals from the laser diode 30-1 do not normally strike the light sensor. The light sensor 30-7 however, detects some of the light scattered by the smoke particles 6, and converts the light signal into an electrical signal. Electronic circuitry 40, 42 in the detector transmits an electrical signal to the control panel or unit 12.

A 5 Milliwatt laser ROHM model No. RLD-78MAT1 is usable as the source 30-1 in the detector 30. The lens 30-2 is a focusing lens.

FIG. 4 is identical to FIG. 3 except that no smoke particles are present in the housing. Instead, dust particles 7, which are relatively large compared to beam diameter and relatively sparse, are shown present at several points in the air of the detector chamber. Because of their low density, a dust particle only enters the relatively small light beam volume on rare occasions. As a consequence, noise due to dust particles can be distinguished from smoke.

A single dust particle 8 is shown in this infrequent position, and scatters a large amount of the light, some of which is detected by the light sensor 30-7. The dust particles are constantly in motion because of small air currents in the chamber. Because of this motion, the dust particle 8 may only reside in the light beam for a short period of time.

The sensor 30-7 generates a transient signal for dust particles. The time that the particle 8 resides in the light beam is equal to the width of the beam in the direction of particle travel, divided by the average velocity of the particle.

As is known, the light source 30-1 will be activated by short pulses every few seconds. As a result, it is often the case that a dust particle will result in the sensor 30-7 generating only a single output noise pulse.

Figure 5:
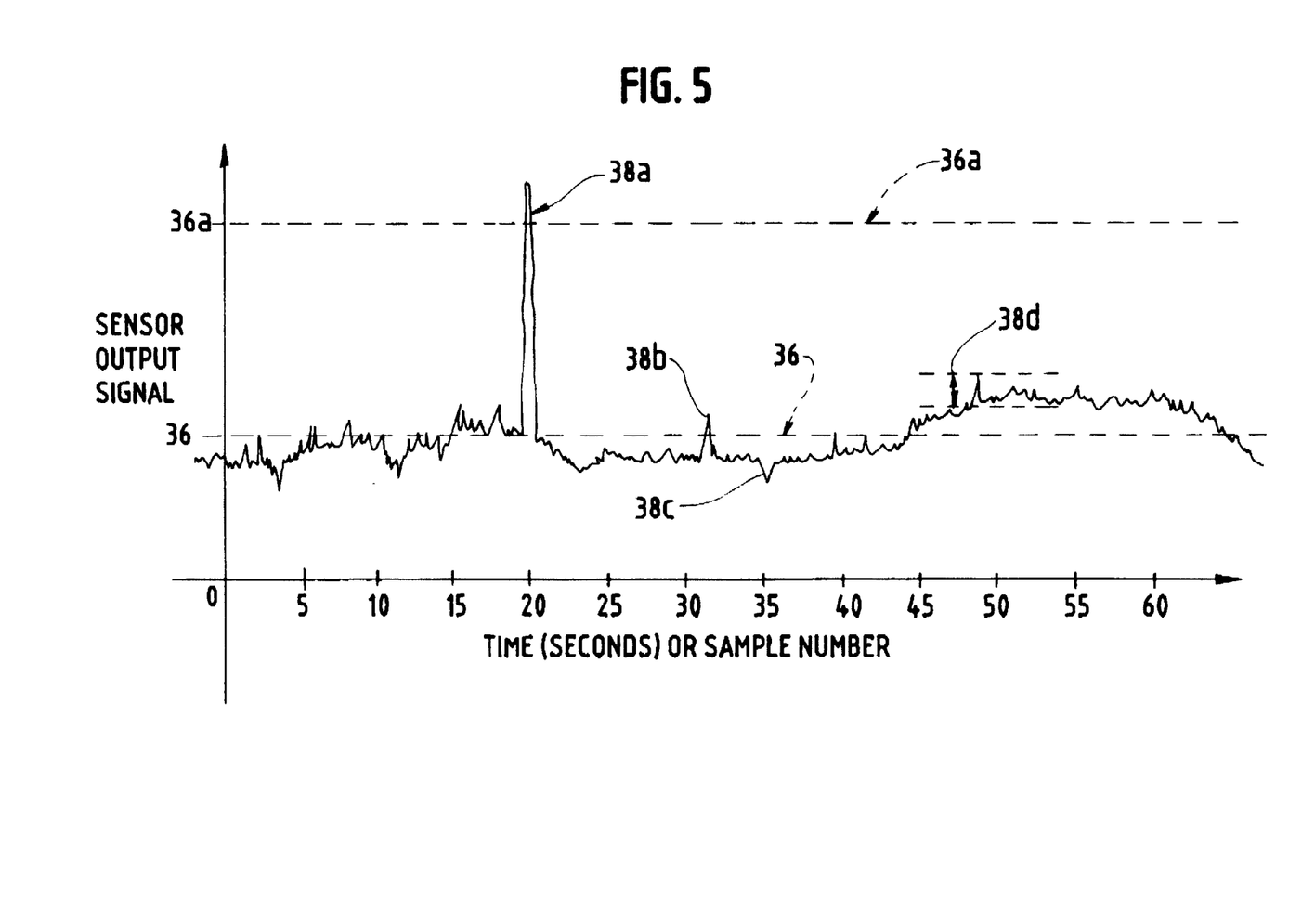
FIG. 5 is a graph of the output of a detector, such as the detector of FIG. 3, as a function of time or sample number in the absence of an ambient condition to be sensed.

FIG. 5 is a representation of an output electrical signal on a line or lines 32, from a sensor 30 in which a dust particle has passed through the detector light beam. This is the raw signal as received directly from a single smoke detector over many samples. The signal on the line or lines 32 can be sampled and transmitted via interface 42 and link 20, to control unit 12.

The line 36a indicates an alarm threshold signal level, at which the control panel 12 would normally indicate an alarm condition.

As is also illustrated on FIG. 5, the sensor 30 produces on the line or lines 32 random noise, indicated by pulses such as pulses 38a, 38b. These pulses which in FIG. 5 are not correlated with any ambient condition to be sensed, such as smoke, fire or temperature, represent the presence of random noise to which the sensor 30 responds.

Typical sources of such noise include dust, insects, transient electrical conditions to which the sensor 30 might respond and the like. The pulses 38a–38b, are uncorrelated with any ambient condition to be detected, such as smoke, heat or fire. As a result, these signals represent undesirable variations which if unaddressed, could conceivably create false alarming in high sensitivity systems.

A DC bias or clear air value 36 exists which is caused by background light reflections, aging of components, and other long term effects. In addition, noise 38c, exists on the waveform because of relatively high frequency electrical interference.

As a result of extensive experiments with prior art detectors, such as the type of detector illustrated in FIG. 2A, it has been determined that in the presence of dust particles, such detectors exhibit smooth output signals which could be mistaken for the presence of smoke. On the other hand, detectors of the type illustrated in FIG. 2B when exposed to similar dust environments produce only transient output signals in response to the dust, comparable to the signals 38A, 38B of FIG. 5. This is because the distance between dust particles appears to be large are relative to the dimensions of the light beam 30-3.

Figure 6:
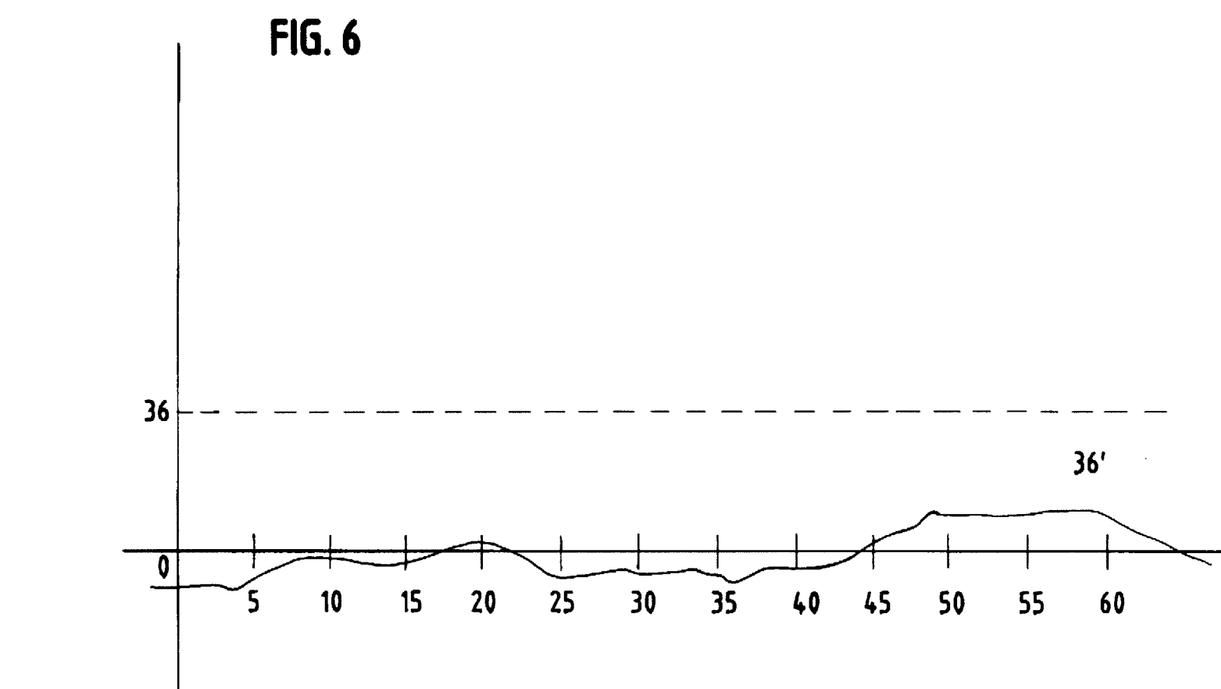
FIG. 6 is a graph of a processed representation of the sensor signal output from the detector illustrated in FIG. 3.

FIG. 6 is a representation of a processed electrical signal 36'. The signal 36' is a processed representation of the signal 36 of FIG. 5. Processing can take place in the control panel 12. The processing could also be done locally in the respective detector. The control unit or panel 12 includes microprocessor 14 and associated control programs which process the received representations of the signal from the sensor 30 to remove the non-fire signals, creating the waveform 36' as shown in FIG. 6.

The light source 30-1 in the chamber is activated every few seconds. The control unit 12 samples the detector at the same approximate rate.

The processor 14 first removes the DC bias or clear air shown as 36 in FIG. 5. This bias is caused by long term effects, such as dust buildup on the surfaces of the detector chamber, making them reflect more light and absorb less light. This is achieved by using a long-term (about 1 day) running average to slowly approximate the DC level of the received waveform for each detector.

At each sample, the long term running average is allowed to move by a very small percentage toward the present reading. Similar comments would apply to outputs from representative sensors such as radiant energy sensors, temperature sensors, or other types of ambient condition sensors without limitation.

A second level or processing is used to remove the effects of the dust transient signals, such as the pulse 38a in FIG. 5. In one embodiment, if the present reading is above the alarm threshold, 36a, the processor 14 compares the present reading of the smoke sensor with the previous reading and accepts the lowest of the two readings as the revised present reading. This allows the system to eliminate any single large sample.

A further improvement to this level of processing is to use the lowest of the present reading compared with the two previous readings. This allows elimination of two large dust pulses in a row, which may occur in unusual situations.

A third level of processing may be used to smooth the signal to remove higher frequency noise as shown by 38c, d in FIG. 5. This noise may be present because of extraneous electrical signals that are conducted or radiated into the detector, or because of noise generated by the electronics of the detector itself.

The sensitivity of each detector is adjustable to take into account low levels of smoke. The processing of the signals automatically increases the amount of smoothing as the sensitivity is increased. While increased smoothing can introduce delays in detection, by elimination of uncorrelated noise, the detectors can be operated at higher levels of sensitivity. Hence, slow burning fires can be detected sooner.

The smoothing processing decreases the degree of smoothing if the received signals are decreasing. For high sensitivities, this smoothing function increases noise rejection at the expense of delay. For low sensitivities, it reduces noise rejection in order to reduce delay to alarm.

This third level of processing also changes the degree of smoothing depending on whether the received detector signal is falling or rising. If falling, the degree of smoothing is decreased, resulting in a more rapid decay of the smoothed signal. This provides faster recovery to small noise pulses, and tends to reduce overall sensitivity during high noise situations.

The control software in combination with digital processor 14 process the signal received from the detectors in accordance with the following:

Level 1.

Drift compensation is achieved for detector 22$n$ by calculating a long term running average value $VA_n$ from the present reading or output value of the detector $V_n$ at a time or sample number t, and a long term constant LC (LC is a very small number such as 0.0001)

$$VA_{nt}=LC*V_{nt}+(1-LC)*VA_{nt-1}$$

A differential, or delta value $$V_{\Delta nt}=(V_{nt}-VA_{nt})$$

Level 2

$V_{\Delta nt}$ is compared with previous detector readings at sample (t-1) and (t-2), and the smallest of the three is selected.

IF $V_{\Delta nt}>(V_n-VA_n)_{t-1}$, THEN $V_{\Delta nt}=(V_n-VA_n)_{t-1}$

IF $V_{\Delta nt}>(V_n-VA_n)_{t-2}$, THEN $V_{\Delta nt}=(V_n-VA_n)_{t-2}$

If the present delta reading $V_{\Delta n,t}$ is less than a pre-established alarm threshold ($AC_n$), the reading is converted back to that reading. This prevents delay for slow rising signals indicative of smoke.

IF $(V_n-VA_n)<AC_n$, THEN $VA_{\Delta n}=(V_{nt}-VA_n)$

Level 3.

A smoothing factor $SF_n$ is established based on the present sensitivity selection $S_n$ (1 through 9) to give continuous progression of smoothing factors. For example, If $S_n=1$, $SF_n=0.04$. If $S_n=9$, $SF_n=0.50$. If readings are declining, the smoothing factor is set to the largest value, for example 0.50. $S_n=1$ is a maximum sensitivity.

IF $V_{\Delta n}\geq VS_n$, THEN $SF_n=0.06*S_n-0.02$, ELSE $SF_n=0.5$

The following is a listing of sensitivity level $S_n$ number (1-most sensitive, 9 is least) versus Smoothing Constant $SF_n$. The smoothing constant calculated as $SF_n=0.06*S_n-0.02$.

| $S_n$ | $SF_n$ |
|---|---|
| 1 | 0.04 |
| 2 | 0.10 |
| 3 | 0.16 |
| 4 | 0.22 |
| 5 | 0.28 |
| 6 | 0.34 |
| 7 | 0.40 |
| 8 | 0.46 |
| 9 | 0.52 |

The smoothing constant $SF_n$ specifies the percentage of the present sample to be added to the previous smoothed value (after multiplying the smoothed value by $1-SF_n$). Therefore, a smaller smoothing constant causes more smoothing than a larger smoothing constant.

The smoothed value of the signal for each detector $VS_n$ is calculated at each sample by adding a small percentage based on the smoothing factor $SF_n$ to a larger percentage of the previous smoothed value.

$$VS_{nt}=SF_n*V_{\Delta nt}+(1-SF_n)*VS_{nt-1}$$

An alarm is detected by the system if the smoothed value $VS_n$ exceeds a stored alarm threshold level $AC_n$ based on a current sensitivity level $S_n$.

IF $VS_n>AC_n$, THEN SET ALARM, ELSE EXIT

Multiple thresholds could be used to indicate pre-alarm conditions if desired.

The processing illustrated in FIG. 6 can be carried out in either the local control element 40 or the system control unit 12. As illustrated by FIG. 6, the individual noise pulses such as 38$a$, 38$b$ have been almost completely eliminated.

In accordance with the second level of processing, the present sensor output, on the line 32, is compared to the previous sensor output, from a prior sample time. The minimum of the two values is selected as the present output value. In the event that the present sensor output value exceeds the minimum of the two values, it is replaced in the pre-processed output stream with the minimum value. Hence, a single noise pulse such as the pulse 38$a$ (FIG. 5) will be completely removed by processing in accordance with the present invention.

The second level of processing in one form can be represented by the following:

if output $_{N-1}$ is greater than output $_N$ then, set output $_N$=to output $_N$, else output $_N$=output $_{N-1}$.

Thus, using the above processing method, the noise will be substantially removed. However, the response to smoke, heat or fire condition will not be significantly reduced. This response will be delayed but only on the order of one to two sample intervals. This delay can be more than offset in that the sensitivity of each of the detectors for the system 10 can significantly increased due to the removal of the transient noise conditions by use of the present preprocessing method. As such, the system 10 should respond to a fire condition faster, since it can operate with detectors set at a higher sensitivity than would be the case where the sensitivity of the detectors had to be reduced to minimize false alarm problems caused by transient noise.

The second level of processing can be enhanced by first, selecting the minimum value between the present value and the previous value, assuming the present value exceeds the nominal value 36 which would be expected in the absence of the ambient condition being sensed and in the absence of noise. In addition, selecting the maximum value between the present sensor value and the previous sensor value in the event that the present sensor value is less than the nominal, noise free output 36 will minimize negative going noise sensors. The above steps will eliminate both positive going and negative going noise pulses.

Figure 7A:
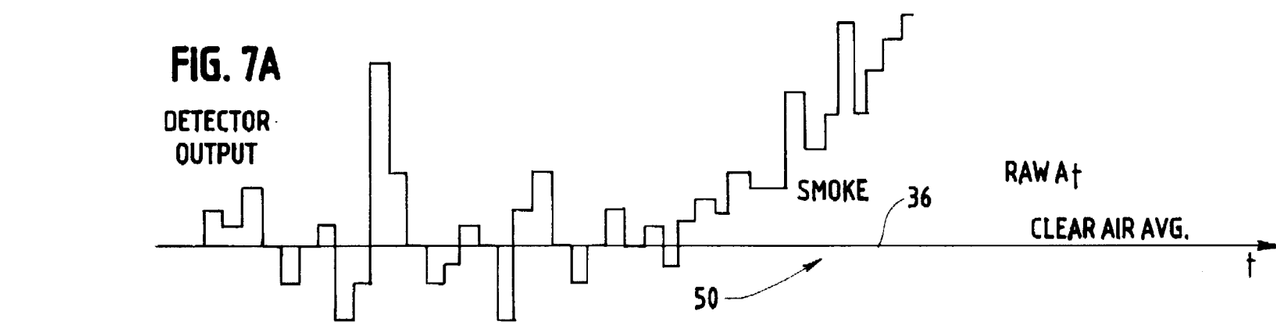
FIGS. 7a–7c are a set of graphs illustrating sensor signal output as well as processed variations thereof.
Figure 7B:
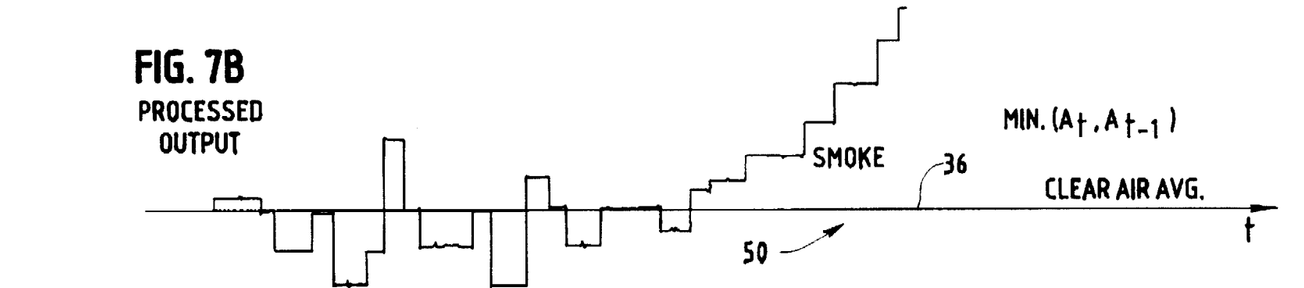
Figure 7C:
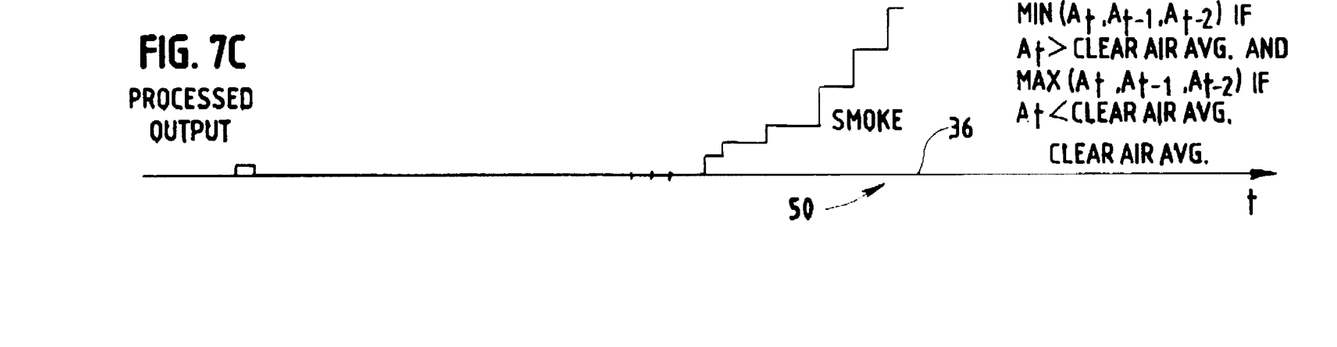

Other variations of level two processing are possible without departing from the spirit and scope of the present method. For example, graphs 7A, 7B and 7C illustrate level two processing using one or two prior output values from the sensor 30.

FIG. 7A illustrates schematically sample values from the sensor 30 on the line 32 as a function of sample number or interval as those values vary about the nominal output value 36. In the region 50, the level of sensed smoke is increasing in a non-random fashion in response to smoke being sensed.

FIG. 7B illustrates level two processing of the signal of FIG. 7A where a minimum of the present output value and one prior output value is selected. As illustrated in FIG. 7B in the presence of smoke, illustrated in region 50, this level two processing method provides a smoothed output indicative of the smoke to be detected.

In accordance with another aspect of the method, the present output value from the sensor 30 can be compared to two previously sensed and stored output values. If the present output value exceeds the threshold 36, a minimum value is determined among the present output value, as well as two prior sample values. The minimum is then substituted, in the pre-processed output stream, for the present output value. In the event that either of the prior samples have values below the nominal output threshold 36, they will be treated as if their value was zero.

If the present output value from the sensor 30 is below the nominal output value 36, the present value will be compared to two prior values and the maximum of the three values will be taken as the present output value. In the event that either of the prior output values is equal to or greater than the nominal output threshold 36, that value(s) will be set to zero. Use of two prior values significantly reduced the noise over the use of a single prior value as in FIG. 7B.

FIG. 7C illustrates a level two processed representation of the signal of FIG. 7A wherein a minimum of the present output value, as well as two prior output values is selected (where the present output value exceeds the nominal output threshold 36). Alternately a maximum of the present output value and two prior output values is selected (where the present output value falls below the nominal output threshold 36). As is illustrated in FIG. 7C, the random uncorrelated noise variations of FIG. 7A have been substantially reduced to zero without providing any significant delay in the processed output in a time interval 50 where smoke is present. More than two prior values can be used if desired.

It will be understood that the exact sample interval is not a limitation of the present invention. Those of skill in the art will understand that an appropriately high sample interval should be chosen, in view of the types of sensors involved as well as the expected rates of change of ambient condition. For exemplary purposes only, and without limitation, sample intervals on the order of five to six seconds appear to be sufficiently short where smoke, heat or fire conditions are being sensed.

Figure 8:
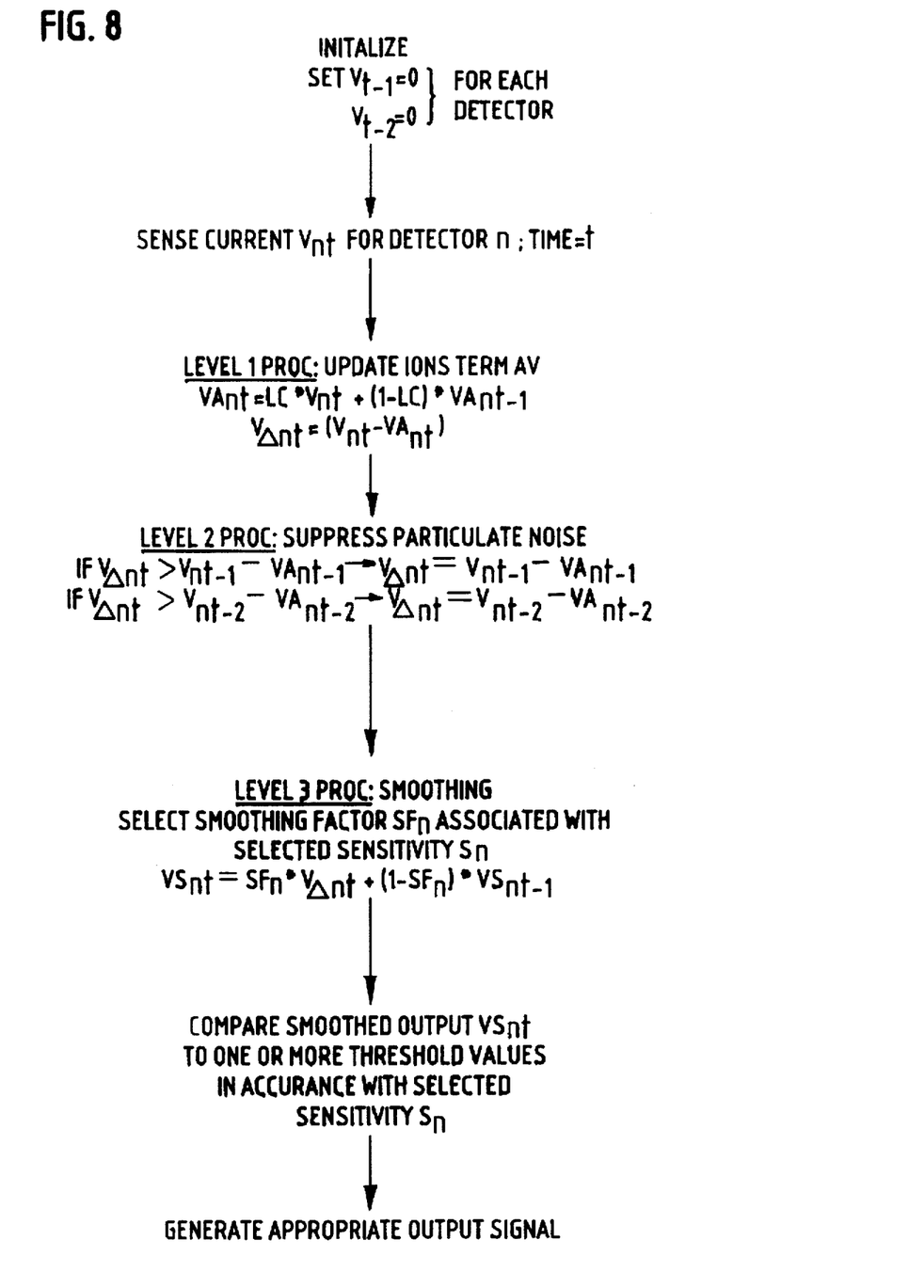
FIG. 8 is a flow diagram illustrating steps associated with level 1 processing, level 2 processing and level 3 processing.

FIG. 8 illustrates a flow diagram of a method in accordance with the present invention.

Figure 9:
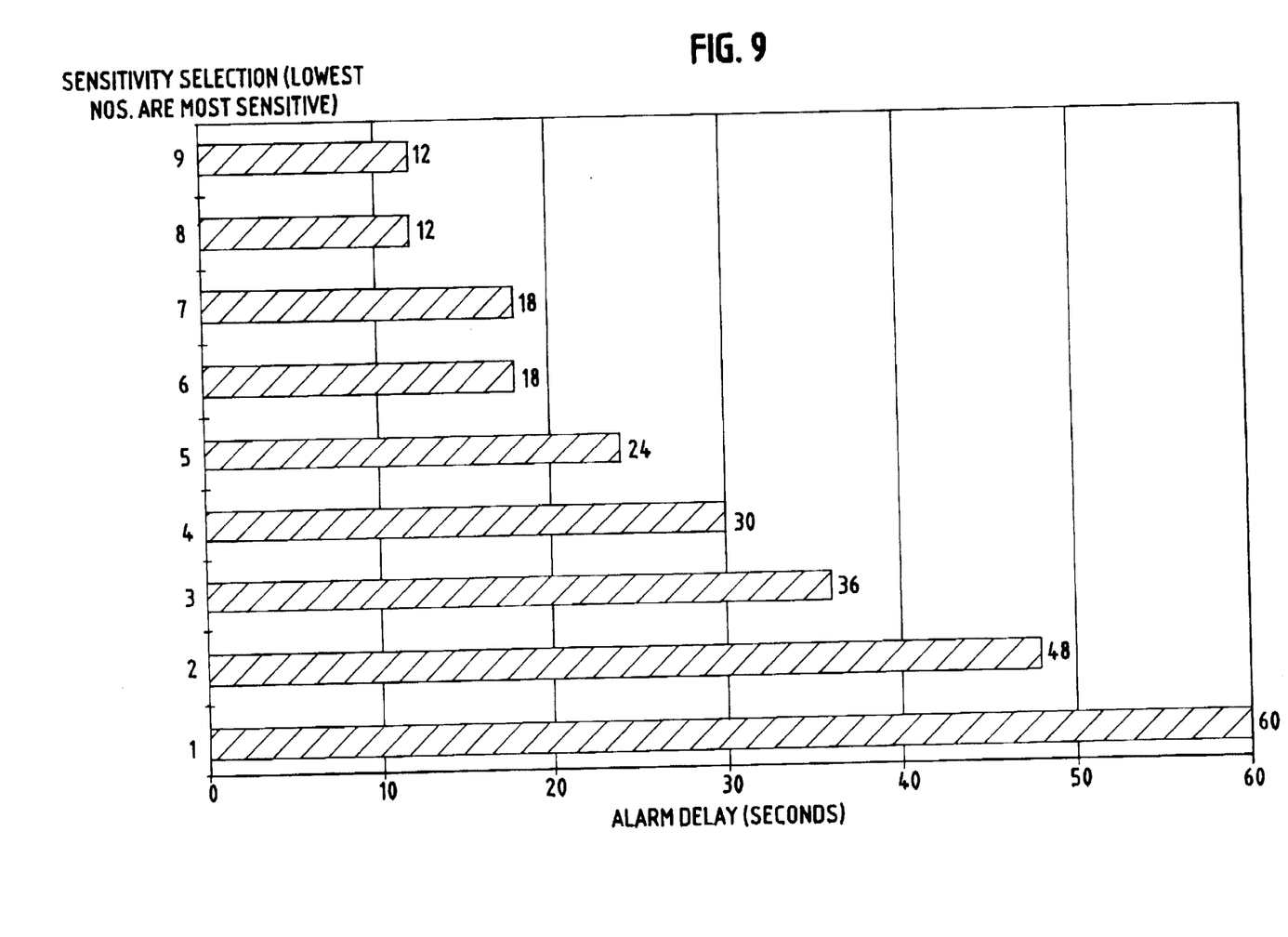
FIG. 9 is a bar chart illustrating alarm delay vs. sensitivity selection.

FIG. 9 is a graph which illustrates the effects of increasing the amount of smoothing in the level 3 processing as a function of increasing the sensitivity of a given detector. The alarm delay in seconds is plotted along the x-axis for decreasing levels of sensitivity which are plotted along the y-axis.

As is illustrated in FIG. 9, a maximum sensitivity setting will generate an alarm delay on the order of 60 seconds as a result of a maximum amount of smoothing. On the other hand, a minimal sensitivity setting will generate an alarm delay on the order of only 12 seconds illustrating a lesser level of smoothing.

The graph of FIG. 9 makes clear that when operating a detector at the highest levels of sensitivity, there is additional delay present before an alarm condition will be detected. On the other hand, detectors which are operating at the highest levels of sensitivity, tend to be more likely to false alarm. The additional delay reduces the potential for false alarms.

Detectors operating with high levels of sensitivity, which are then processed as described above with greater level of smoothing, are especially useful in detecting slowly progressing or smoldering fires. Such fires often take minutes or even hours to reach high levels. In this instance, the 48 second or 60 second delays illustrated in FIG. 9, are often a very small portion of the total time necessary to detect such a fire.

On the other hand, fires which are progressing at a rapid rate can often be detected at lower levels of sensitivity due to rapidly increasing smoke levels. In such instances there is little chance of dust or other noise causing a false alarm. In such circumstances, the short 12 and 18 second delays illustrated in FIG. 9 are consistent with a desire to report the presence of such fires as soon as possible.

From the foregoing, it will be observed that numerous variations and modifications may be effected without departing from the spirit and scope of the invention. It is to be understood that no limitation with respect to the specific apparatus illustrated herein in tended or should be inferred. It is, of course, intended to cover by the appended claims all such modifications as fall within the scope of the claims.

We claim:

1. A fire detection and alarm system comprising:
   at least one photoelectric smoke detector having a housing, a source carried by said housing, a sensing light beam projected into said housing wherein said beam has dimensions smaller than a typical distance between ambient dust particles and wherein said detector transmits a signal in response to dust particles of a first, transient frequency and transmits a signal in response to the presence of smoke of a second, lower frequency;
   a control unit which receives said signals from said smoke detector and which includes a computer section and an alarm signaling section and;
   a control program stored within said computer section of said control unit whereby said program processes the signals from said smoke detector, and which activates said alarm signaling section when signals are received which are caused by a predetermined level of smoke in said smoke detector, but does not activate said alarm section when signals are received which are caused by dust particles in said smoke detector.

2. A system as in claim 1 wherein the determination of alarm signals caused by smoke particles is said smoke detector and not caused by dust particles is said smoke detector can be used to lower a required magnitude of signals received by said control unit in order to activate said signaling section.

3. A system as in claim 1 wherein said control program periodically samples said smoke detector and differentiates between smoke and dust signals by comparing a present sample with a previous sample and replacing said present sample with said previous sample if said previous sample is lower in magnitude than said present sample.

4. A system as in claim 1 wherein said control program periodically samples a signal from said smoke detector and differentiates between smoke and dust signals by comparing a present sample from said smoke detector with a plurality of previous signal samples from said smoke detector and replacing said present sample with the lowest of said previous several samples if said previous several samples are lower in magnitude than said present sample.

5. A system as in claim 4 wherein said signal from said smoke detector is processed by said control program to remove long-term drift caused by dust on the chamber surfaces, component aging, or other very low frequency changes by subtracting a long term running average value from an absolute value of the signal received from said smoke detector.

6. A system as in claim 1 which includes a focusing lens positioned adjacent to said source for said beam, in the path of said beam, a sensor carried by said housing wherein said source and said sensor are spaced apart less than three inches from one another.

7. A fire detection and alarm system comprising:

at least one photoelectric smoke detector having a housing, a source carried by said housing, a sensing light beam projected into said housing wherein said beam has dimensions smaller than a typical distance between ambient dust particles and wherein said detector transmits signals that are a measurement of smoke concentration within the detector;

a control unit which receives said signals from said smoke detector and which includes a computer section and an alarm signaling section and;

a control program stored within said computer section of said control unit whereby said program processes the signals from said smoke detector, and which activates said alarm signaling section when signals are received which are caused by a predetermined level of smoke particles in said smoke detector, but does not activate said alarm section when signals are received which are caused by dust in said smoke detector, wherein said signal received from said smoke detector is processed by said control program and is converted into a present smoothed signal by adding a percentage of a present signal sample to a percentage of a smoothed signal value calculated from a previous signal sample from said smoke detector to create said present smoothed value.

8. A system as in claim 7 wherein said control program is programmed to select one of a plurality of different reference signal levels for said smoke detector necessary to cause activation of said alarm signaling section, and wherein when said control program selects a lower signal reference level, said smoothed signal calculation is altered to use smaller percentage of said present sample and a larger percentage of the previous smoothed signal to calculate the new smoothed signal.

9. A system as in claim 8 wherein said control program determines if the present signal sample from said smoke detector is less than a smoothed value calculated from a previous sample of said smoke detector, and if so, the smoothed signal calculation is altered to use a larger percentage of said present sample and a smaller percentage of the previous smoothed signal to calculate the new smoothed signal.

10. An alarm system comprising:

a plurality of smoke detectors;

a bidirectional communications link coupled to said detectors; and a control element coupled to said link wherein said element includes control circuitry for establishing a respective sensitivity for each of said detectors along with a respective signal smoothing parameter wherein as said sensitivity increases for a respective detector, said smoothing parameter is changed to provide an increased level of smoothing thereby reducing dust induced indications of smoke for the respective detector.

11. An alarm system as in claim 10 wherein at least some of said detectors include photoelectric smoke sensors.

12. An alarm system as in claim 11 wherein said photoelectric sensors include an internal effective beam volume in a range of 0.005 to 0.008 cubic inches.

13. An alarm system as in claim 11 wherein said photoelectric sensors include an effective beam volume on the order of 0.0067 cubic inches.

14. An alarm system comprising:

a plurality of photoelectric smoke sensors;

a bidirectional communications link coupled to said smoke sensors;

a control element coupled to said link wherein said element includes control circuitry for establishing a respective sensitivity for each of said detectors along with a respective signal smoothing parameter wherein as said sensitivity increases for a respective detector, said smoothing parameter is increased and wherein in response thereto, said control element processes an output signal from a respective one of said sensors with a correspondingly increased level of smoothing thereby injecting an increased delay into a determination of the presence of a fire condition.

15. A fire detection and alarm system comprising:

at least one photoelectric smoke detector having a housing which defines an internal volume, a source for generating a sensing light beam which is projected into said internal volume wherein said beam has a sensing region with dimensions smaller than the typical distance between ambient dust particles and a sensor of scattered light which generates electrical signals that are a measure of smoke concentration within the detector wherein the presence of smoke in the volume provides a relatively low frequency signal, and presence of dust provides a relatively transient or high frequency signal;

a control unit which receives said signals from said smoke detector and which includes a computer section and an alarm signaling section and;

a control program stored within said computer section of said control unit whereby said program processes the signals from said smoke detector, and which activates said alarm signaling section when signals are received which are caused by a predetermined level of smoke particles in said smoke detector, but does not activate said alarm section when signals are received which are caused by dust particles in said smoke detector.

16. A system as in claim 15 wherein the determination of alarm signals caused by smoke particles in said smoke detector and not caused by dust particles in said smoke detector can be used to lower a required magnitude of signals received by said control unit in order to activate said signaling section.

17. A system as in claim 15 wherein said control program periodically samples said smoke detector and differentiates between smoke and dust signals by comparing a present sample with a previous sample and replacing said present sample with said previous sample if said previous sample is lower in magnitude than said present sample.

18. A system as in claim 15 wherein said control program periodically samples a signal from said smoke detector and differentiates between smoke and dust signals by comparing a present sample from said smoke detector with a plurality of previous signal samples from said smoke detector and replacing said present sample with the lowest of said previous several samples if said previous several samples are lower in magnitude than said present sample.

19. A system as in claim 18 wherein said signal from said smoke detector is processed by said control program to remove long-term drift caused by dust on the chamber surfaces, component aging, or other very low frequency changes by subtracting a long term running average value from an absolute value of the signal received from said smoke detector.

20. A fire detection and alarm system comprising:
   at least one photoelectric smoke detector having a housing which defines an internal volume, a source for generating a sensing light beam which is projected into said internal volume wherein said beam has a sensing region with dimensions smaller than the typical distance between ambient dust particles and a sensor of scattered light which generates electrical signals that are a measure of smoke concentration within the detector;
   a control unit which receives said signals from said smoke detector and which includes a computer section and an alarm signaling section and;
   a control program stored within said computer section of said control unit whereby said program processes the signals from said smoke detector, and which activates said alarm signaling section when signals are received which are caused by a predetermined level of smoke particles in said smoke detector, but does not activate said alarm section when signals are received which are caused by dust particles in said smoke detector; and
   wherein said signal received from said smoke detector is processed by said control program and is converted into a present smoothed signal by adding a percentage of a present signal value to a percentage of a smoothed signal value calculated from a previous signal sample from said smoke detector to create said present smoothed value.

21. A system as in claim 20 wherein said control program is programmed to select one of a plurality of different reference signal levels for said smoke detector necessary to cause activation of said alarm signaling section, and wherein when said control program selects a lower signal reference level, said smoothed signal calculation is altered to use smaller percentage of said present sample and a larger percentage of the previous smoothed signal to calculate the new smoothed signal.

22. A system as in claim 21 wherein said control program determines if the present signal sample from said smoke detector is less than a smoothed value calculated from a previous sample of said smoke detector, and if so, the smoothed signal calculation is altered to use a larger percentage of said present sample and a smaller percentage of the previous smoothed signal to calculate the new smoothed signal.

23. An alarm system comprising:
   a plurality of smoke detectors;
   a bidirectional communications link coupled to said detectors; and
   a control element coupled to said link wherein said element includes control circuitry for establishing a plurality of sensitivity levels and a plurality of respective smoothing parameters wherein a respective, programmable sensitivity level is set for each of said detectors along with a respective signal smoothing parameter wherein as said respective sensitivity increases for a respective detector, said smoothing parameter is changed to provide an increased level of smoothing thereby reducing dust induced indications of smoke for the respective detector.

24. An alarm system as in claim 23 wherein at least some of said detectors include cylindrical housings which carry photoelectric smoke sensors.

25. An alarm system as in claim 24 wherein said photoelectric sensors include an internal effective beam volume of less than 0.008 cubic inches.

26. An alarm system as in claim 24 wherein said photoelectric sensors include an effective beam volume on the order of 0.0067 cubic inches.

27. An alarm system as in claim 25 wherein each of said photoelectric sensors includes a housing having a largest size parameter which is less than three inches.

28. An event detection system comprising:
   at least one photoelectric smoke detector having a housing, a source carried by said housing, a sensing light beam projected into said housing wherein said beam has dimensions smaller than a typical distance between ambient dust particles and wherein said detector transmits signals that are an indication of smoke concentration within the detector, and wherein the signals may include transient values produced by the presence of dust in the housing;
   a control unit which receives said signals from said smoke detector and which includes circuitry for processing the signals from said smoke detector by storing a selected plurality of prior values of the signals and comparing a current value to the prior stored values and circuitry for selecting a minimum value as a current processed signal value.

29. A system as in claim 28 wherein the control unit includes a read-write storage unit for storage of at least two prior values of the signals.

30. A system as in claim 29 wherein the control unit includes circuitry for converting the present processed signal value to a present smoothed signal value by adding a percentage of the present processed signal value to a percentage of a prior smoothed signal value to a percentage of a prior smoothed signal value determined from a prior signal value.

31. A fire detection and alarm system comprising:
   at least one photoelectric smoke detector having a housing, a source carried by said housing, a sensing light beam projected into said housing wherein said beam has dimensions smaller than a typical distance between ambient dust particles and wherein said detector transmits signals that are a measurement of smoke concentration within the detector;
   a control unit which receives said signals from said smoke detector and which includes a computer section and an alarm signaling section and;
   a control program stored within said computer section of said control unit whereby said program processes the signals from said smoke detector, and which activates said alarm signaling section when signals are received which are caused by a predetermined level of smoke particles in said smoke detector, but does not activate said alarm section when signals are received which are caused by dust particles in said smoke detector;
   wherein said control program differentiates between smoke and dust signals from said smoke detection device in response to the presence of smoke providing a relatively constant or low frequency signal, and dust providing a relatively transient or high frequency signal;
   wherein said control program periodically samples a signal from said smoke detector and differentiates between smoke and dust signals by comparing a present sample from said smoke detector with a plurality of previous signal samples from said smoke detector and replacing said present sample with the lowest of said previous several samples if said previous several samples are lower in magnitude than said present sample;
   wherein said signal from said smoke detector is processed by said control program to remove long-term drift caused by dust on the chamber surfaces, component aging, or other very low frequency changes by subtracting a long term running average value from an absolute value of the signal received from said smoke detector; and wherein said signal received from said smoke detector is processed by said control program and is converted into a present smoothed signal by adding a percentage of said present signal sample to a percentage of a smoothed signal value calculated from a previous signal sample from said smoke detector to create said present smoothed value.

* * * * *